US011970687B2

(12) United States Patent
Jourdainne et al.

(10) Patent No.: US 11,970,687 B2
(45) Date of Patent: Apr. 30, 2024

(54) INSTALLATION FOR TREATING BIOLOGICAL LIQUID

(71) Applicant: EMD Millipore Corporation, Burlington, MA (US)

(72) Inventors: Laurent Jourdainne, Stutzheim-Offenhein (FR); Sebastien Cirou, Hochstati (FR)

(73) Assignee: EMD Millipore Corporation, Burlington, MA (US)

( * ) Notice: Subject to any disclaimer, the term of this patent is extended or adjusted under 35 U.S.C. 154(b) by 473 days.

(21) Appl. No.: 17/262,957

(22) PCT Filed: May 15, 2019

(86) PCT No.: PCT/US2019/032376
§ 371 (c)(1),
(2) Date: Jan. 25, 2021

(87) PCT Pub. No.: WO2020/023104
PCT Pub. Date: Jan. 30, 2020

(65) Prior Publication Data
US 2021/0253994 A1   Aug. 19, 2021

(30) Foreign Application Priority Data

Jul. 27, 2018 (EP) ..................................... 18306016

(51) Int. Cl.
*C12M 1/34* (2006.01)
*C12M 1/12* (2006.01)
*C12M 3/00* (2006.01)

(52) U.S. Cl.
CPC ............ *C12M 41/26* (2013.01); *C12M 23/44* (2013.01); *C12M 37/00* (2013.01)

(58) Field of Classification Search
CPC ....... C12M 41/26; C12M 23/44; C12M 37/00
(Continued)

(56) References Cited

U.S. PATENT DOCUMENTS 8,916,045 B2 * 12/2014 Reinbigler ............. C12M 23/44
210/260
2005/0239198 A1 * 10/2005 Kunas .................... C12M 23/26
435/297.1
(Continued)

FOREIGN PATENT DOCUMENTS

CN      103443262 A     12/2013
CN      104395341 A      3/2015
(Continued)

OTHER PUBLICATIONS

WO2016059925-A1 Description Machine English Translation (Year: 2016).*
(Continued)

*Primary Examiner* — Michael L Hobbs
*Assistant Examiner* — Lenora A Abel
(74) *Attorney, Agent, or Firm* — EMD Millipore Corporation

(57) ABSTRACT

The invention concerns an installation for treating biological liquid by viral inactivation, comprising a main supply valve (4) for suppling biological liquid to treat, a first line (2) downstream of said valve and provided with a first main tank (7), a second line (3) downstream of said valve and provided with a second main tank (14), said second line being in parallel with said first line, and a third main tank (11) disposed at an outlet both from said first line and said second line and configured to be successively supplied by said first main tank and by said second main tank; said installation being configured such that in each of said first, second and third main treatment tanks, a determined volume of acid and a determined volume of base are introduced at least so as to adjust a pH of said biological liquid and to regulate a rate of drainage flow of said third main treatment tank so as to
(Continued)

provide a continuous rate of flow of treated biological liquid at an outlet from said installation.

15 Claims, 4 Drawing Sheets

(58) Field of Classification Search
USPC .................................................... 435/289.1
See application file for complete search history.

(56) References Cited

U.S. PATENT DOCUMENTS

| | | |
|---|---|---|
| 2012/0248025 A1 | 10/2012 | Reinbigler et al. |
| 2018/0228927 A1 | 8/2018 | Ito et al. |
| 2021/0253994 A1 | 8/2021 | Jourdainne et al. |

FOREIGN PATENT DOCUMENTS

| | | |
|---|---|---|
| CN | 107794221 B | 7/2022 |
| EP | 2682168 A1 | 1/2014 |
| EP | 3290507 A1 | 3/2018 |
| EP | 3599275 A1 | 1/2020 |
| EP | 3830241 A1 | 6/2021 |
| FR | 2961711 A1 | 12/2011 |
| FR | 2973396 A1 | 10/2012 |
| JP | 2013-534822 A | 9/2013 |
| JP | 2014-509521 A | 4/2014 |
| JP | 2015-522019 A | 8/2015 |
| JP | 2016-077190 A | 5/2016 |
| WO | 2012/131562 A1 | 10/2012 |
| WO | 2014/004281 A1 | 1/2014 |
| WO | WO-2016059925 A1 * | 4/2016 ............. A61K 35/76 |

OTHER PUBLICATIONS

International Search Report and Written Opinion received for PCT Patent Application No. PCT/US2019/032376, mailed on Aug. 19, 2019, 9 pages.

Office Action received for Korean Patent Application No. 10-2021-7005800, mailed on Sep. 23, 2022, 17 Pages (8 Pages of English Translation & 9 Pages of Official Copy).

Office Action received for Korean Patent Application No. 10-2021-7005800, mailed on Jul. 17, 2022, 17 Pages (8 Pages of English Translation & 9 Pages of Official Copy).

First Examination Report received for Indian Application No. 202117001130 mailed on Sep. 5, 2022, 6 Pages.

Office Action received for Japanese Patent Application No. 2021-504341, mailed on Mar. 29, 2022, Pages 10 (6 Pages of English Translation & 4 Pages of Official Copy).

Office Action received for Canadian Patent Application No. 3,105,489 mailing date Nov. 8, 2023, 5 pages.

Communication pursuant to Article 94(3) EPC received for European Patent Application No. 19727262.8 mailing date Jan. 30, 2024, 5 Pages.

Office Action received for Chinese Patent Application No. 201980050153.8 mailing date Dec. 29, 2023, 15 Pages (7 Pages of English translation & 8 Pages of official copy).

* cited by examiner

INSTALLATION FOR TREATING BIOLOGICAL LIQUID

CROSS-REFERENCE TO RELATED APPLICATIONS

The present application is a US National Stage application of International Application No. PCT/US2019/032376, filed May 15, 2019, which claims the benefit of priority of EP Application No. 18306016.9, filed Jul. 27, 2018, the entire content of each of which are incorporated by reference herein in its entirety.

FIELD OF THE INVENTION

The invention relates to installations for treating biological liquid, in particular but not exclusively for the viral inactivation of a biopharmaceutical liquid.

TECHNOLOGICAL BACKGROUND

Biopharmaceutical liquids are in general obtained by cultures in a bioreactor and they must then be purified to achieve the required characteristics of purity, concentration, absence of viruses, etc.

The purification may be carried out by means of a succession of treatments such as clarification to eliminate the residues from the bioreactor culture, elution by chromatography to separate proteins, viral inactivation then polishing and/or purification by tangential filtration or by chromatography.

It is desirable to carry out the above steps continuously or semi-continuously, one after the other. However, these treatment steps do not all take the same time and it is sometimes necessary to stop certain treatments while one or more other treatments are being finished. In particular, it is known that the treatment time for viral inactivation generally requires an incubation time while the flow of product is stopped.

Patent application EP 2 682 168 relates to a viral inactivation treatment and describes a process in which a flow is fractioned into small volumes of product, also called fractions. This process enables viral inactivation which is particularly fast, for each of the small fractions (or volumes) of product, one after the other.

A viral inactivation installation is also known that comprises a central distributor supplied with product to treat, with acid and with base, and which is configured to direct different streams of product, acid and base, including two streams which are referred to as treatment streams, to two respective tanks, and a stream which is referred to as an outlet stream outletting either to a drain or to an outlet pipe for treated product. The installation is furthermore provided with two recirculation loops for the two treatment streams each provided between a respective tank and the central distributor.

SUBJECT OF THE INVENTION

The invention aims to provide an installation enabling the simple, convenient and economical implementation of a viral inactivation treatment for a biological liquid.

For this, according to a first aspect, the invention concerns an installation for treating biological liquid by viral inactivation, characterized in that it comprises:
- a main supply valve for supplying biological liquid to treat, configured to be connected to at least one source of biological liquid supply;
- a first treatment line downstream of said supply valve and provided with a first main treatment tank configured to be supplied by said supply valve with biological liquid to treat;
- a second treatment line downstream of said supply valve and provided with a second main treatment tank configured to be supplied by said supply valve with biological liquid to treat;
- said second treatment line being in parallel with said first treatment line; and
- a third main treatment tank disposed at an outlet both from said first treatment line and from said second treatment line and which is configured to be successively supplied by said first main treatment tank and by said second main treatment tank;
- said installation is configured such that in each of said first, second and third main treatment tanks, a determined volume of acid and a determined volume of base are introduced at least so as to adjust a pH of said biological liquid; and said installation is also configured to regulate a rate of drainage flow of said third main treatment tank so as to provide a continuous rate of flow of treated biological liquid at an outlet from said installation.

In other words, in the biological liquid treatment installation according to the invention, the third main treatment tank is common to the first and second treatment lines.

The first and second treatment lines thus extend in parallel from the main supply valve to the third main treatment tank.

What is more, in the biological liquid treatment installation according to the invention, the third main treatment tank makes it possible to finish the treatment of the biological liquid already treated in the first main treatment tank or in the second main treatment tank. In particular, the third main treatment tank may be provided to pre-polish the biological liquid, that is to say in order for the latter to reach a target pH. Once the third main treatment tank has been filled with treated biological liquid and once the pre-polishing has been carried out, the third main treatment tank empties with a controlled and continuous rate of flow.

It is to be noted that such pre-polishing enables the biological liquid to be prepared for a later polishing step of that liquid, for example using a chromatography treatment.

According to other preferred simple, convenient and economical features of the installation according to the invention:
- said first treatment line is provided with a first intermediate treatment tank disposed between said first and third main treatment tanks;
- said installation is configured in order for a determined volume of acid and for a determined volume of base to be introduced into said first intermediate treatment tank;
- said installation is configured in order for said biological liquid treated in said first main treatment tank to be transferred into said first intermediate treatment tank and incubates for a predetermined time in the latter, before its transfer into said third main treatment tank;
- said second treatment line is provided with a second intermediate treatment tank disposed between said second and third main treatment tanks;
- said installation is configured in order for a determined volume of acid and for a determined volume of base to be introduced into said second intermediate treatment tank;
- said installation is configured in order for said biological liquid treated in said second main treatment tank to be transferred into said second intermediate treatment tank and incubates for a predetermined time in the latter, before its transfer into said third main treatment tank;

said installation comprises a plurality of supply pumps disposed on said first and second treatment lines, at least between said first main treatment tank and said third main treatment tank, and possibly between said first main treatment tank and said first intermediate treatment tank and/or between said first intermediate treatment tank and said third main treatment tank; and at least between said second main treatment tank and said third main treatment tank, and possibly between said second main treatment tank and said second intermediate treatment tank and/or between said second intermediate treatment tank and said third main treatment tank;

said determined volumes of acid, and respectively said determined volumes of base, introduced at least into said first, second and third main treatment tanks, and possibly into said first and second intermediate treatment tanks, depend on the physico-chemical properties of the biological liquid to treat and may be equal or different;

at least said first, second and third main treatment tanks, and possibly said first and second intermediate treatment tanks, are provided with a stirrer for biological liquid and/or with one or more instrumentation members.

said installation comprises one or more control and command units configured to control and command said supply valve and/or at least one of said first, second and third main treatment tanks, and possibly to control and command said first and second intermediate treatment tanks;

said installation comprises a single cart on which are disposed at least said supply valve, said first, second and third main treatment tanks, and possibly said first and second intermediate treatment tanks; and/or said installation is provided with disposable pipes, referred to a single-use pipes, linking different parts composing it, including at least said supply valve, said first, second and third main treatment tanks, and possibly said first and second intermediate treatment tanks.

According to a second aspect, the invention also concerns a process for treating biological liquid by viral inactivation, using a treatment installation as described above, said process comprising:

a step of at least partial filling with biological liquid to treat of a first main treatment tank of a first treatment line of said installation via a main supply valve of said installation;

a step of adjusting pH of said biological liquid by introducing a determined volume of acid and a determined volume of base into said first main treatment tank;

a step of incubating said biological liquid in said first treatment line for a predetermined time and a step of adjusting pH of said biological liquid by introducing a determined volume of acid and a determined volume of base into said first treatment line to approach a target pH;

a step of transferring said treated biological liquid into a third main treatment tank of said installation disposed at an outlet from said first treatment line, and a step of pre-polishing by introducing a determined volume of acid and a determined volume of base into said third main treatment tank to obtain a treated biological liquid at the target pH;

at the same time as the steps of pre-polishing and/or transfer and/or incubation and/or adjustments of pH implemented in said first treatment line, a step of at least partial filling with biological liquid to treat of a second main treatment tank of a second treatment line of said installation via said main supply valve, said second treatment line being in parallel with said first treatment line;

a step of adjusting pH of said biological liquid by introducing a determined volume of acid and a determined volume of base into said second main treatment tank;

a step of incubating said biological liquid in said second treatment line for a predetermined time and a step of adjusting pH of said biological liquid by introducing a determined volume of acid and a determined volume of base into said second treatment line to approach a target pH;

a step of transferring said treated biological liquid into said third main treatment tank also disposed at an outlet from said second treatment line, and a step of pre-polishing by introducing a determined volume of acid and a determined volume of base into said third main treatment tank to obtain a treated biological liquid at the target pH;

at the same time as the steps of pre-polishing and/or of transferring and/or incubating and/or adjusting pH implemented in said second treatment line, a step of draining said third main treatment tank by regulating a draining rate of flow so as to provide a continuous rate of flow of treated biological liquid at an outlet from said installation.

According to other preferred, simple, convenient and economical features of the treatment process according to the invention, said first treatment line is provided with a first intermediate treatment tank disposed between said first and third main treatment tanks and said second treatment line is provided with a second intermediate treatment tank disposed between said second and third main treatment tanks; and the process comprises a step of transferring said biological liquid from said first main treatment tank to said first intermediate treatment tank and the steps of incubating and adjusting pH to approach a target pH in said first treatment line take place in said first intermediate treatment tank; as well as a step of transferring said biological liquid from said second main treatment tank to said second intermediate treatment tank and the steps of incubating and adjusting pH to approach a target pH in said second treatment line take place in said second intermediate treatment tank;

BRIEF DESCRIPTION OF THE DRAWINGS

The disclosure of the invention will now be continued with the description of an embodiment, given below by way of illustrative and non-limiting example, with reference to the accompanying drawings, in which.

DETAILED DESCRIPTION OF AT LEAST ONE EMBODIMENT

Figure 1:
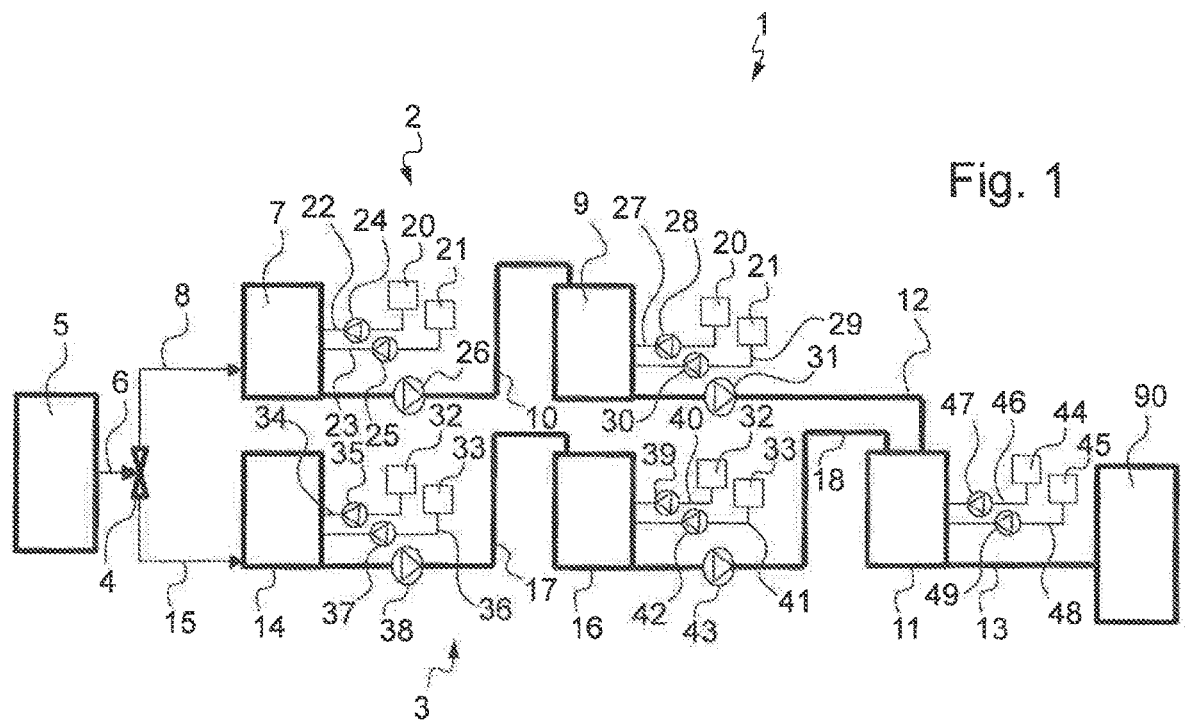
FIG. 1 diagrammatically represents a treatment installation in accordance with the invention.

FIG. 1 diagrammatically illustrates an installation for biological liquid 1 treatment by virus inactivation.

The installation comprises a first treatment line 2 and a second treatment line 3 which extends in parallel with the first treatment line 2.

The installation 1 may further comprise, upstream of said first and second treatment lines 2 and 3, a source 5 of biological liquid supply and a main supply valve 4 for biological liquid to treat connected to the source 5 of biological liquid supply via a first pipe 6.

It is to be noted that this supply source may be directly connected to an outlet pipe of a treatment line of an installation upstream of the installation 1; or else an individual container connected or not connected to such an upstream installation.

The first treatment line 2 may be provided with a first main treatment tank 7 configured to be supplied with biological liquid to treat by the supply valve 4 via a second pipe 8, and with a first intermediate treatment tank 9 disposed downstream of the first main treatment tank 7 and connected to the latter via a third pipe 10.

The second treatment line 3 may be provided with a second main treatment tank 14 configured to be supplied with biological liquid to treat by the supply valve 4 via a fourth pipe 15, and with a second intermediate treatment tank 16 disposed downstream of the second main treatment tank 14 and connected to the latter via a fifth pipe 17.

The installation 1 may also comprise, downstream of the first and second treatment lines 2 and 3, an outlet line mainly formed here by a third main treatment tank 11 which is connected to the first intermediate treatment tank 9 via a sixth pipe 12, and which is also connected to the second intermediate treatment tank 16 via a seventh pipe 18.

Thus, the first intermediate treatment tank 9 is interposed between the first main treatment tank 7 and the third main treatment tank 11; whereas the second intermediate treatment tank 16 is interposed between the second main treatment tank 14 and the third main treatment tank 11.

The third main treatment tank 11 is disposed at an outlet from both the first and second treatment lines 2 and 3 and is configured to be successively supplied by the first main treatment tank 7 and by the second intermediate treatment tank 16.

In other words, the third main treatment tank 11 is common to the first and second treatment lines 2 and 3.

The first and second treatment lines 2 and 3 extend in parallel from the main supply valve 4 to the third main treatment tank 11.

The installation 1 may be configured in order for the biological liquid treated in the first main treatment tank 7, and respectively in the second main treatment tank 14, to be transferred into the first intermediate treatment tank 9, and respectively into the second intermediate treatment tank 16, and incubates for a predetermined time in the latter, prior to its transfer into the third main treatment tank 11.

For this the installation 1 may comprise a first main supply pump 26 mounted on the third pipe 10 and configured to drain the first main treatment tank 7 and transfer the biological liquid treated in the latter to the first intermediate treatment tank 9; as well as a first intermediate supply pump 31 mounted on the sixth pipe 12 and configured to drain the first intermediate treatment tank 9 and transfer the biological liquid treated in the latter to the third main treatment tank 11.

The installation 1 may further comprise a second main supply pump 38 mounted on the fifth pipe 17 and configured to drain the second main treatment tank 14 and transfer the biological liquid treated in the latter to the second intermediate treatment tank 16; as well as a second intermediate supply pump 43 mounted on the seventh pipe 18 and configured to drain the second intermediate treatment tank 16 and transfer the biological liquid treated in the latter to the third main treatment tank 11.

The installation 1 may also be configured such that a determined volume of acid and a determined volume of a base is introduced into each of the first, second and third main treatment tanks 7, 14 and 11 and each of the first and second intermediate treatment tanks 9 and 16, so as to adjust a pH of the biological liquid.

For this the installation 1 may comprise a first tank for an acid 20 which is connected to the first main treatment tank 7 via an eighth pipe 22 on which is mounted a first acid pump 24, and which is also connected to the first intermediate treatment tank 9 via a ninth pipe 27 on which is mounted a second acid pump 28.

The installation 1 may also comprise a first tank for a base 21 which is connected to the first main treatment tank 7 via an tenth pipe 23 on which is mounted a first base pump 25, and which is also connected to the first intermediate treatment tank 9 via an eleventh pipe 29 on which is mounted a second base pump 30.

The installation 1 may further comprise a second tank for an acid 32 which is connected to the second main treatment tank 14 via a twelfth pipe 34 on which is mounted a third acid pump 35, and which is also connected to the second intermediate treatment tank 16 via a thirteenth pipe 40 on which is mounted a fourth acid pump 39.

The installation 1 may additionally comprise a second tank for a base 32 which is connected to the second main treatment tank 14 via a fifteenth pipe 36 on which is mounted a third base pump 37, and which is also connected to the second intermediate treatment tank 16 via a sixteenth pipe 41 on which is mounted a fourth base pump 42.

The installation 1 may also comprise a third reservoir for an acid 44 which is connected to the third main treatment tank 11 via a seventeenth pipe 46 on which is mounted a fifth acid pump 47, and a third tank for base 45 which is connected to the third main treatment tank 11 via an eighteenth pipe 48 on which is mounted a fifth base pump 49.

It will be noted that the third main treatment tank 11 may be drained by means of an outlet pipe 13, which is connected to a circuit 90 (represented very diagrammatically) in an installation disposed downstream of the installation 1. This circuit 90 may be configured to implement a step of polishing the biological liquid, for example by chromatography.

All the pipes 6, 8, 10, 12, 13, 15, 17, 18, 22, 23, 27, 29, 34, 36, 40, 41, 46 and 48 may for example be flexible disposable pipes, referred as single-use pipes.

It will also be noted that the installation 1 is configured here to regulate at least one rate of flow for drainage of the third main treatment tank 11 so as to provide a continuous rate of flow of treated biological liquid at an outlet from the installation 1 (see below). The rate of flow value depends on the circuit 90 upstream of the installation 1 and on the treatment implemented, here polishing of the biological liquid.

A description will now be given, with reference to FIG. 2, of a process for treating biological liquid by viral inactivation, using the treatment installation 1 described above.

Figure 2:
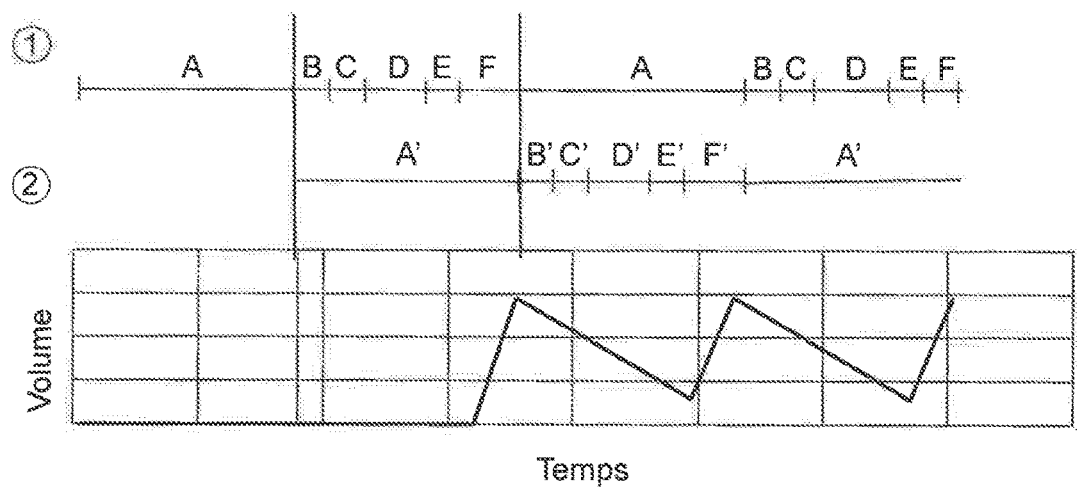
FIG. 2 is a time chart showing different steps of a treatment process using the installation of FIG. 1.

In particular, FIG. 2 represents, in the manner of a time diagram, on its first line, different steps implemented on the first treatment circuit 2, on its second line, different steps implemented on the second treatment line 3, and on its third line, the volume of biological liquid in the third main treatment tank 11.

The process for treating biological liquid by viral inactivation, using the treatment installation 1 comprises the steps below.

The process may comprise a step of at least partial filling A with biological liquid to treat of the first main treatment tank 7 via the main supply valve 4 and the second pipe 8.

The filling time depends on the volume of the first main treatment tank 7.

The process may comprise a step B of adjusting pH of the biological liquid present in the first main treatment tank 7 by introducing a determined volume of acid and a determined volume of base into that first main treatment tank 7, via the eighth pipe 22 and the first acid pump 24 and via the tenth pipe 23 and the first base pump 25.

The volumes of acid and base depend on the pH value of the biological liquid inlet to the first main treatment tank 7.

The process may comprise a step of incubating the biological liquid in the first treatment line 2 for a predetermined time and a step of adjusting pH of the biological liquid by introducing a determined volume of acid and a determined volume of base into the first treatment line 2 to approach a target pH.

It is to be noted that the target pH may correspond to a neutral pH or else be different from a neutral pH. The target pH depends on the type of treatment implemented in the circuit 90 in the installation which comes after the installation 1.

In particular, the process may comprise a step C of transferring the biological liquid from the first main treatment tank 7 to the first intermediate treatment tank 9 via the first main supply pump 26 and the third pipe 10; a step D of incubating the biological liquid in the first intermediate treatment tank 9; and a step E of adjusting pH to approach a target pH, by introducing a determined volume of acid and a determined volume of base into that first intermediate treatment tank 9, via the ninth pipe 27 and the second acid pump 28 and via the eleventh pipe 29 and the second base pump 30.

The process may comprise a step F of transferring the treated biological liquid from the first intermediate treatment tank 9 to the third main treatment tank 11 via the first intermediate supply pump 31 and the sixth pipe 12.

At the same time as the transfer step F, and subject to having transferred a sufficient determined volume, the process may comprise a step of pre-polishing of the biological liquid in the third main treatment tank 11, by introducing a determined volume of acid and a determined volume of base into the third main treatment tank 11, via the seventeenth pipe 46 and the fifth acid pump 47 and via the eighteenth pipe 48 and the fifth base pump 49; to obtain a treated biological liquid at the target pH.

Steps A to F described above concern the first treatment line 2. In parallel with steps B to F, that is to say after filling the first main treatment tank 7, the process may comprise at the same time the following steps.

The process may comprise a step of at least partial filling A' with biological liquid to treat of the second main treatment tank 14 via the main supply valve 4 and the fourth pipe 15.

The filling time depends on the volume of the second main treatment tank 14. Here, the volumes of the first and second main treatment tanks 7 and 14 are identical.

The process may comprise a step B' of adjusting pH of the biological liquid present in the second main treatment tank 14 by introducing a determined volume of acid and a determined volume of base into that second main treatment tank 14, via the twelfth pipe 34 and the third acid pump 35 and via the fifteenth pipe 36 and the third base pump 37.

The volumes of acid and base depend on the pH value of the biological liquid inlet to the second main treatment tank 14.

The process may comprise a step of incubating the biological liquid in the second treatment line 3 for a predetermined time and a step of adjusting pH of the biological liquid by introducing a determined volume of acid and a determined volume of base into the second treatment line 3 to approach a target pH.

In particular, the process may comprise a step C' of transferring the biological liquid from the second main treatment tank 14 to the second intermediate treatment tank 16 via the second main supply pump 38 and the fifth pipe 17; and a step D' of incubating the biological liquid in the second intermediate treatment tank 16; and a step E' of adjusting pH to approach a target pH, by introducing a determined volume of acid and a determined volume of base into that second intermediate treatment tank 16, via the thirteenth pipe 40 and the fourth acid pump 39 and via the sixteenth pipe 41 and the fourth base pump 42.

The process may comprise a step F' of transferring the treated biological liquid from the second intermediate treatment tank 16 to the third main treatment tank 11 via the second intermediate supply pump 43 and the seventh pipe 18.

At the same time as the transfer step F', and also subject to having transferred a sufficient determined volume, the process may comprise a step of pre-polishing of the biological liquid in the third main treatment tank 11, by introducing a determined volume of acid and a determined volume of base into the third main treatment tank 11, via the seventeenth pipe 46 and the fifth acid pump 47 and via the eighteenth pipe 48 and the fifth base pump 49; to obtain a treated biological liquid at the target pH.

Steps A' to F' described above concern the second treatment line 3. In parallel with steps B' to F', that is to say after filling the second main treatment tank 14, the process may again implement the step A of filling the first main treatment tank 7 then steps B to F and so forth, as can be seen in FIG. 2.

FIG. 2 also shows that the process can comprise the step of draining the third main treatment tank 11 when the latter has been filled by the first treatment line 2 and the biological liquid has been pre-polished therein.

The drainage of the third main treatment tank 11 is made at a regulated rate of flow and may last approximately the duration of steps B' to E' that are implemented in the second treatment line 3, after which the third main treatment tank 11 may again be filled but by the second treatment line 3, and so forth. It will be noted that the third main treatment tank 11 may never be fully emptied once it has been filled.

The regulation of the outlet rate of flow from the third main treatment tank 11 makes it possible to provide a continuous rate of flow of treated biological liquid at an outlet from the installation 1.

Figure 3:
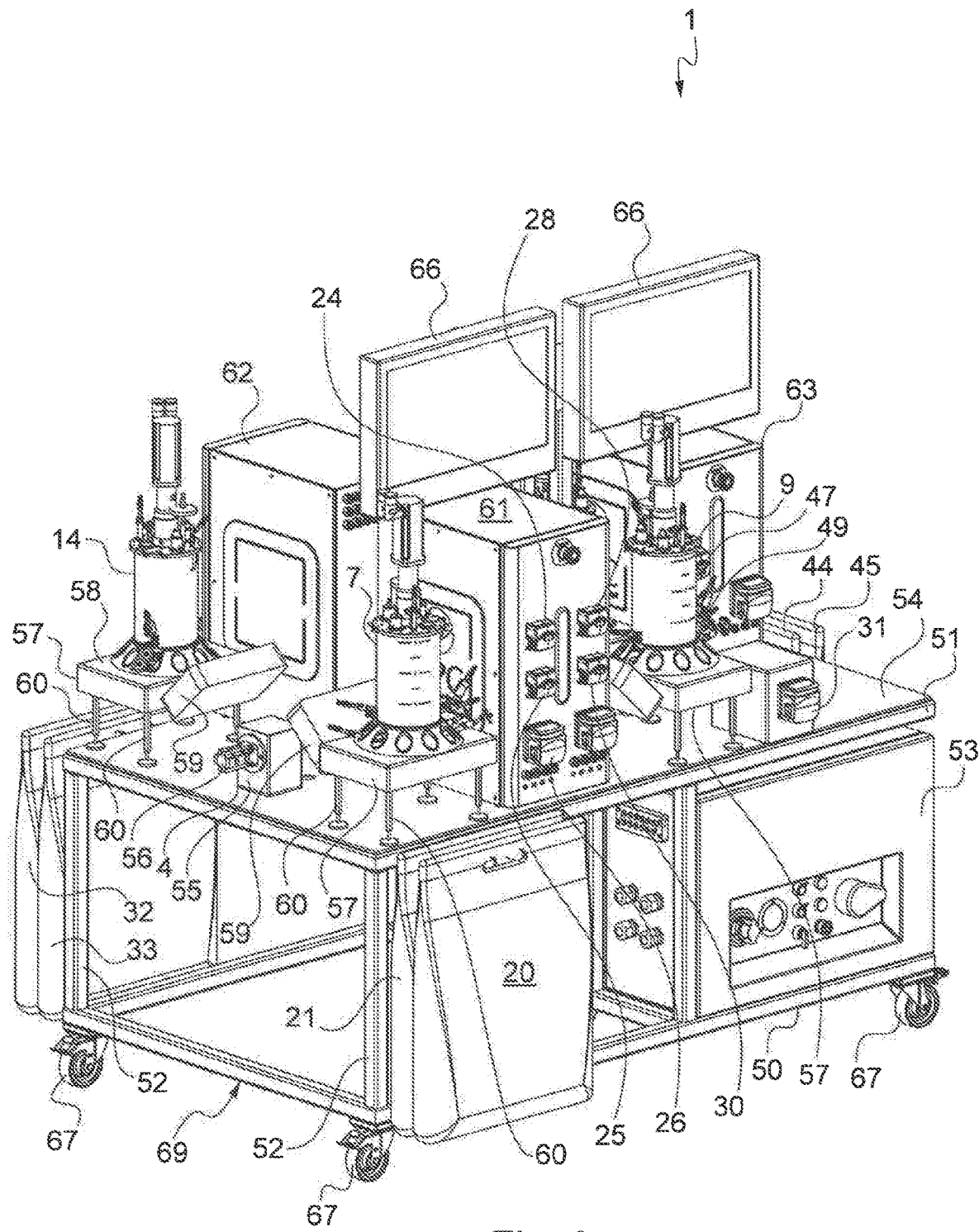
FIGS. 3 to 5 are views in perspective and from above of the treatment installation of FIG. 1.
Figure 4:
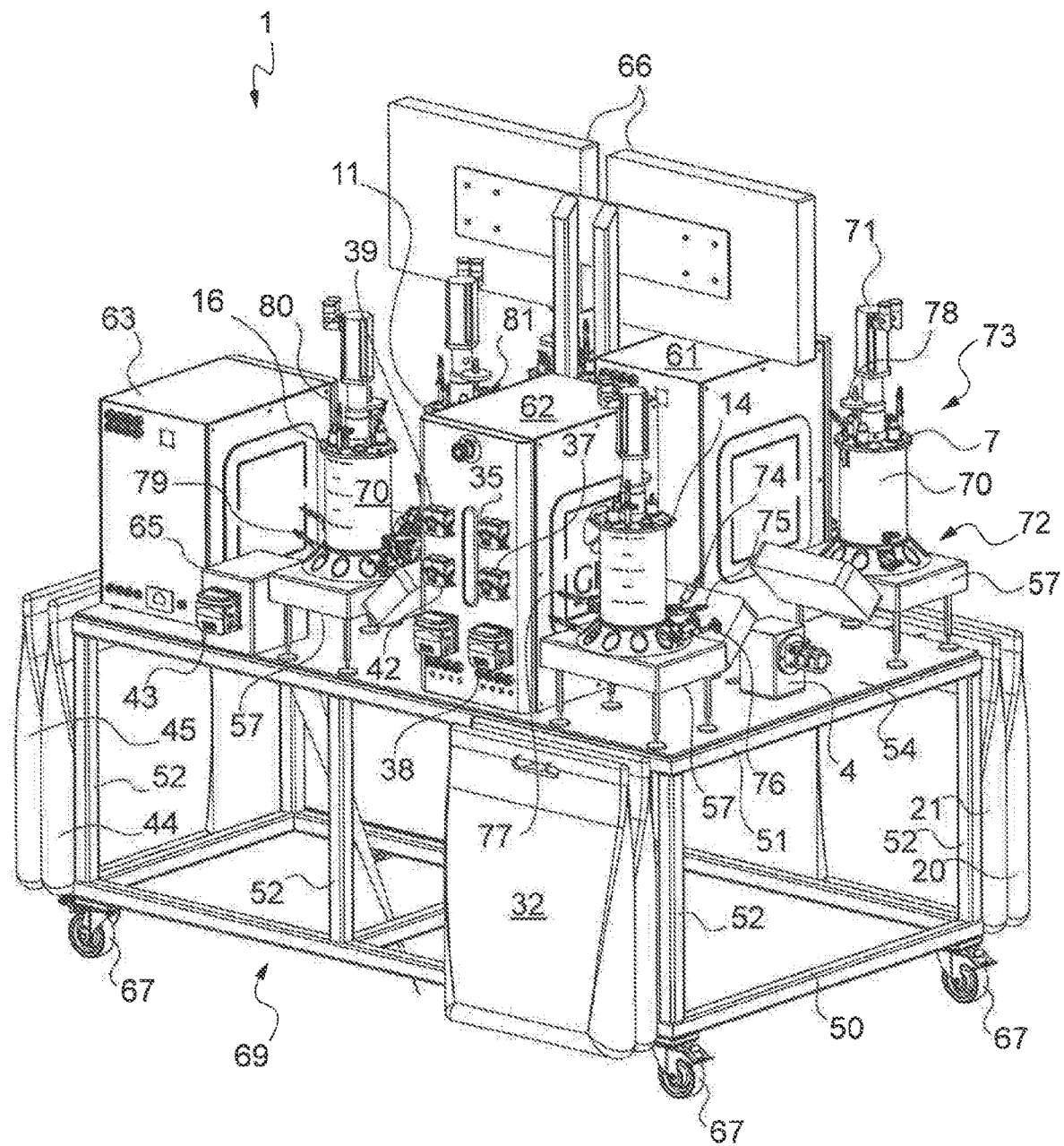
Figure 5:
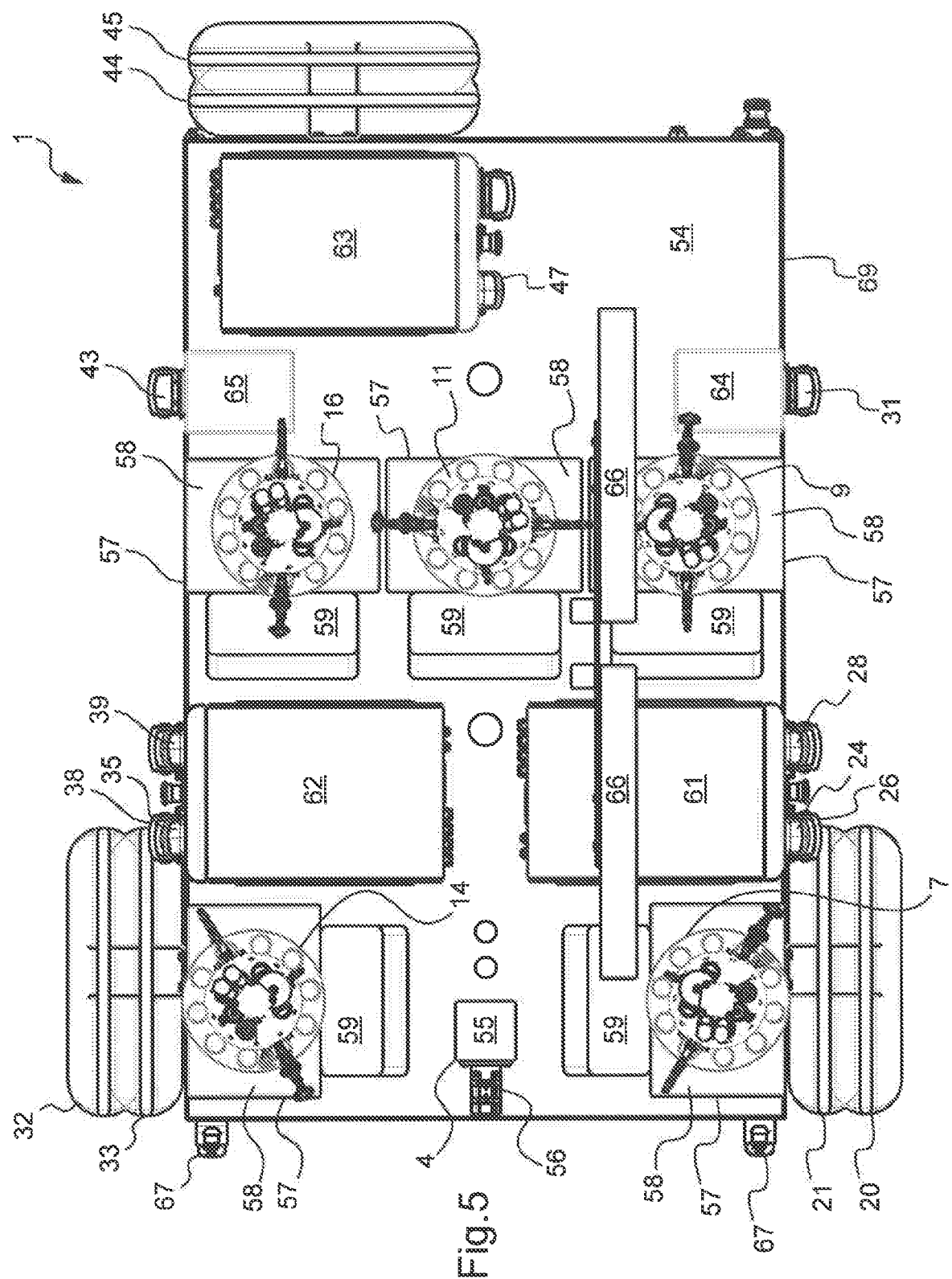

A description will now be given in more detail, with reference to FIGS. 3 to 5, of the arrangement of the installation 1 itself and of its components, which in the embodiment illustrated here are carried by a single cart 69.

The cart 69 may be formed by a framework, of which a lower frame 50 is mounted on castors 67, an upper frame 51 is at a distance from the lower frame 50, and vertical upright members 52 extending between the lower frame 50 and the upper frame 51, and by a plate 54 jointed to the upper frame 51.

The installation 1 may comprise a pneumatic and electrical supply general unit 53 placed on the lower frame 50.

The cart 69 may have a parallelepiped general shape.

The first tanks of acid 20 and 21 may be suspended, at the location of the upper frame 51, on a first side of the cart 69.

The second tanks of acid 32 and 33 may be suspended, at the location of the upper frame 51, on a second side of the cart 69 which is an opposite side to the first side.

The third tanks of acid 44 and base 45 may be suspended, at the location of the upper frame 51, on a third side of the cart 69 linking its first and second sides, at an outlet from the installation 1.

All these tanks may be formed by flexible bags. It is to be noted that the source of supply is not visible in FIGS. 3 to 5.

The supply valve 4 may be placed on the plate 54 at the location of a fourth side of the cart 69, also linking the first and second sides and being an opposite side to the third side.

The supply valve 4 may be a three-way valve, comprising two inlets and one outlet or one inlet and two outlets.

The valve 4 may for example have a head 56 for example provided with two grooves for receiving portions of pipes and a pinch mechanism configured to allow or prevent the passage of biological liquid in the portions of pipes received in the two grooves; and a body 55 provided with a pneumatic actuator configured to actuate the pinch mechanism.

The first and second main treatment tanks 7 and 14 may be disposed on the plate 54 at the location of the fourth side of the cart 69 and on respective opposite sides of the supply valve 4.

Thus, the first main treatment tank 7 may be located on the first side of the cart 69 while the second main treatment tank 14 is located on the second side of the cart 69.

The first and second main treatment tanks 7 and 14 may both be mounted on respective weighing scales 57, each provided with feet 60 on which is installed a weighing scales plate 58 and a device 59 for control and command of the weighing scales 59.

The first and second main treatment tanks 7 and 14 may be mounted directly on the weighing scales plates 58.

The installation 1 may comprise a first control and command unit 61 and a second control and command unit 62 which may be disposed on the plate 54 respectively near the first and second main treatment tanks 7 and 14.

The first control and command unit 61 may be provided with a body from which partly project the first acid pump 24, the first base pump 25, the first main supply pump 26, the second acid pump 28 and the second base pump 30, from the first side of the cart 69.

The second control and command unit 62 may be provided with a body from which partly project the third acid pump 35, the third base pump 37, the second main supply pump 38, the fourth acid pump 39 and the fourth base pump 42, from the second side of the cart 69.

The first and second control and command units 61 and 62 may thus be configured to control and actuate the aforementioned pumps to implement at least the steps B and B' of adjusting pH within the first and second main treatment tanks 7 and 14, steps C and C' of transferring within the first and second treatment lines 2 and 3, steps D and D' of incubating and E and E' of adjusting pH in the first and second intermediate treatment tanks 9 and 16.

The first and second intermediate treatment tanks 9 and 16 may be disposed on the plate 54, with the first and second control and actuation units 61 and 62 which are located interposed between the first and second intermediate treatment tanks 9 and 16 and the first and second main treatment tanks 7 and 14.

The first intermediate treatment tank 9 may be located on the first side of the cart 69 while the second intermediate treatment tank 16 is located on the second side of the cart 69.

The first and second intermediate treatment tanks 9 and 16 may both be mounted on respective weighing scales 57, like the first and second main treatment tanks 7 and 14, which are provided with feet, with a weighing scales plate 58 and with a device 59 for control and command of the weighing scales. The first and second intermediate treatment tanks 9 and 16 may be mounted directly on the weighing scales plates 58.

The installation 1 may comprise transfer devices 64 and 65 disposed on the plate 54 respectively near the first and second intermediate treatment tanks 9 and 16, and which respectively project from the first intermediate supply pump 31 of the first side of the cart 69 and the second intermediate supply pump 43 of the second side of the cart 69.

These transfer devices 64 and 65 may thus be configured to control and actuate the aforementioned pumps to implement steps F and F' of transferring the treated biological liquid from the first and second treatment lines 2 and 3 to the third main treatment tank 11 in the outlet line.

The third main treatment tank 11 may be interposed between the first and second intermediate treatment tanks 9 and 16.

The third main treatment tank 11 may be mounted on weighing scales 57, like the first and second main treatment tanks 7 and 14 and like the first and second intermediate treatment tanks 9 and 16, which weighing scales are provided with feet, with a weighing scales plate 58 and with a device for controlling and commanding the weighing scales 59. The third main treatment tank 11 is directly mounted on the weighing scales plate 58.

The installation 1 may comprise a third control and command unit 63 disposed on the plate 54 near the third main treatment tank 11 and at the location of the third side of the cart 69.

The third control and command unit 63 may be provided with a body from which partially projects the fifth acid pump 47 and the fifth base pump 49, from the third side of the cart 69.

The third control and actuation unit 63 may thus be configured to control and actuate the aforementioned pumps to implement at least the steps of pre-polishing in the third main treatment tank 11.

The installation 1 may comprise control screens 66 mounted on a fixed mounting projecting from the plate 54 of the cart 69. These control screens 66 may make it possible to view in particular of the advancement of the treatment process described above and to manage the parameters associated with each of the steps of that process.

In the example described with reference to FIGS. 3 to 5, the first, second and third main treatment tanks 7, 14 and 11 and the first and second intermediate treatment tanks 9 and 16 may be formed according to a same structure.

In particular, these tanks may comprise a closed chamber 70, here cylindrical and extending between a lower base 72 and an upper platform 73, as well as a stirring mechanism 71 provided with a motor projecting from the upper platform 73 and with a stirrer (not visible) driven by the motor and extending within the chamber 70.

These tanks may furthermore be provided with a filtering device and/or a vent 78 projecting from the upper platform 73 and instrumentation members (not shown) also projecting from the upper platform 73 and for example formed by a pressure sensor and by a temperature sensor.

These tanks may furthermore be provided with several inlet and/or outlet apertures, situated at the location of the lower base 72 and/or at the location of the upper platform 73 and/or along the chamber 70. The use of these different inlet and/or outlet apertures depends on the function of the tanks.

In particular, the first and second main treatment tanks 7 and 14 may be identical and each comprise a first inlet aperture 77 provided to be supplied with biological liquid and which is situated for example at the bottom of the chamber 70 near the lower base 72, a second inlet aperture 74 provided to be supplied with acid and situated for example at the bottom of the chamber 70 near the lower base 72, a third inlet aperture 75 provided to be supplied with base and situated for example also at the bottom of the chamber 70 near the lower base 72, and an outlet aperture 76 provided for the transfer of the biological liquid to the first intermediate treatment tank 9, and respectively the second intermediate tank 16, and which is situated for example here in the lower base 72.

The first and second intermediate treatment tanks 9 and 16 may be identical and similar to the first and second main treatment tanks 7 and 14, with the exception of a first inlet aperture 80 which is provided here to be supplied with biological liquid from a respective main tank and which for example projects from the upper platform 73, and an outlet aperture 79 which is provided for the transfer of the biological liquid to the third main treatment tank 11 and which is situated for example in the lower base 72.

The third main treatment tank 11 may be very similar to the first and second intermediate treatment tanks 9 and 16, apart from the fact that its first inlet aperture 80 may be provided to be supplied with treated biological liquid from one of the first and second intermediate treatment tanks 9 and 16, that it may comprise a fourth inlet aperture 81 provided to be supplied with treated biological liquid from the other of the first and second intermediate treatment tanks 9 and 16 and which projects from the upper platform 73, and that its outlet aperture 79 may be provided for the transfer of the biological liquid at an outlet from the installation.

In variants that are not illustrated:
it is possible for the installation not to have intermediate treatment tanks, the incubation then taking place in the first and second main tanks;
the steps relative to the second treatment line may be launched before the end of the filling of the first main treatment tank in the first treatment line;
the rate of drainage flow from the third main treatment tank may vary or be fixed, provided there is supplied a continuous stream of treated biological outlet from the installation;
the installation may comprise more than two circuits in parallel, for example three, four or more;
the installation may comprise several outlet tanks common to at least two treatment lines;
the installation may be arranged on several carts which are preferably juxtaposed against each other;
the main and intermediate tanks may be arranged differently from each other and for example be provided with more or fewer instrumentation members;
the main and intermediate tanks may be directly placed on the plate of the cart;
the installation may comprise a single control-command unit or two, or else more than three control and actuation units; and/or
the installation may comprise a single control screen or else more than two control screens.

It should be noted more generally that the invention is not limited to the examples described and represented.

What is claimed:

1. An installation for treating a biological liquid by viral inactivation, comprising
   a main supply valve for supplying a biological liquid to treat, configured to be connected to at least one source of biological liquid supply;
   a first treatment line downstream of the main supply valve, the first treatment line including a first end coupled to the main supply valve, an opposite second end, and a first main treatment tank disposed between the first end and the second end of the first treatment line, the first main treatment tank being configured to be supplied by the main supply valve with the biological liquid to treat;
   a second treatment line downstream of the main supply valve, the second treatment line including a third end coupled to the main supply valve, an opposite fourth end, and a second main treatment tank disposed between the third end and the fourth end of the second treatment line, the second main treatment tank being configured to be supplied by the main supply valve with the biological liquid to treat, wherein the second treatment line is in parallel with the first treatment line; and
   a third main treatment tank disposed at the second end of the first treatment line and the fourth end of the second treatment line and which is further configured to be successively supplied by the first main treatment tank and by the second main treatment tank;
   wherein the installation is configured such that in each of the first, second, and third main treatment tanks, a determined volume of acid and a determined volume of base are introduced at least so as to adjust a pH of the biological liquid; and the installation is also configured to regulate a rate of drainage flow out of the third main treatment tank so as to provide a continuous rate of flow of treated biological liquid at an outlet from the installation.

2. The installation according to claim 1, wherein the first treatment line is provided with a first intermediate treatment tank disposed between the first and third main treatment tanks.

3. The installation according to claim 2, wherein the installation is configured to introduce a determined volume of acid and for a determined volume of base into the first intermediate treatment tank.

4. The installation according to claim 3, wherein the installation is configured in order for the biological liquid treated in the first main treatment tank to be transferred into the first intermediate treatment tank and incubate for a predetermined time in the first intermediate treatment tank, before its transfer into the third main treatment tank.

5. The installation according to claim 4, wherein the second treatment line is provided with a second intermediate treatment tank disposed between the second and third main treatment tanks.

6. The installation according to claim 5, wherein a determined volume of acid and a determined volume of base can be introduced into the second intermediate treatment tank.

7. The installation according to claim 6, wherein the biological liquid treated in the second main treatment tank can be transferred into the second intermediate treatment tank and incubate for a predetermined time in the second intermediate treatment tank, before it is transferred into the third main treatment tank.

8. The installation according to claim 7, wherein a plurality of supply pumps can be placed on the first and second treatment lines, at least between the first main treatment tank and the third main treatment tank, and optionally between the first main treatment tank and the first intermediate treatment tank and/or between the first intermediate treatment tank and the third main treatment tank; and at least between the second main treatment tank and the third main treatment tank, and optionally between the second main treatment tank and the second intermediate treatment tank and/or between the second intermediate treatment tank and the third main treatment tank.

9. An installation according to claim 8, wherein the determined volume of acid and the determined volume of base, are introduced at least into the first, second and third main treatment tanks, and depending on physico-chemical properties of the biological liquid to be treated optionally introduced into the first and second intermediate treatment tanks, wherein the determined volume of acid and the determined volume of base introduced into the first, second, and third main treatment tanks may be equal or different to the determined volume of acid and the determined volume of base added to the first and second intermediate treatment tanks.

10. The installation according to claim 9, wherein the at least first, second and third main treatment tanks, and optionally the first and second intermediate treatment tanks, are provided with a stirrer for biological liquid and/or with one or more instrumentation units.

11. The installation according to claim 10, wherein one or more control and command units can be configured to control and command the main supply valve, the first, second and third main treatment tanks, and optionally the first and second intermediate treatment tanks.

12. The installation according to claim 1, wherein a single cart contains at least the main supply valve, the first, second and third main treatment tanks, and optionally the first and second intermediate treatment tanks.

13. The installation according to claim 12, wherein the main supply valve, the first, second and third main treatment tanks, and optionally the first and second intermediate treatment tanks are linked by disposable pipes.

14. A process for treating biological liquid by viral inactivation, using the installation according to claim 1, the process comprising the steps of:
  at least partial filling the first main treatment tank with biological liquid to treat of from the first treatment line of the installation via the main supply valve of the installation;
  adjusting the pH of the biological liquid by introducing a determined volume of acid and a determined volume of base into the first main treatment tank;
  incubating the biological liquid in the first treatment line for a predetermined time and adjusting the pH of the biological liquid in the first treatment line by introducing a determined volume of acid and a determined volume of base into the first treatment line to approach a target pH;
  transferring the treated biological liquid into the third main treatment tank of the installation disposed at the second end of the first treatment line;
  pre-polishing the biological liquid in the third main treatment tank by introducing a determined volume of acid and a determined volume of base into the third main treatment tank to obtain a final treated biological liquid at the target pH;
  whereas at the same time as the above steps of pre-polishing and/or transfer and/or incubation and/or adjustments of pH implemented in the first treatment line, at least partial filling the second treatment tank with biological liquid to treat via the main supply valve, the second treatment line being in parallel with the first treatment line;
  adjusting the pH of the biological liquid in the second main treatment tank by introducing a determined volume of acid and a determined volume of base into the second main treatment tank;
  incubating the biological liquid in the second treatment line for a predetermined time and adjusting the pH of the biological liquid by introducing a determined volume of acid and a determined volume of base into the second treatment line to approach a target pH;
  transferring the treated biological liquid into the third main treatment tank also disposed at the fourth end of the second treatment line, and pre-polishing the treated biological fluid by introducing a determined volume of acid and a determined volume of base into the third main treatment tank to obtain a final treated biological liquid at the target pH; and
  draining the third main treatment tank by regulating a draining rate of flow so as to provide a continuous rate of flow of treated biological liquid at the outlet from the installation at the same time as pre-polishing and/or of transferring and/or incubating and/or adjusting pH implemented in the second treatment line.

15. The process according to claim 14, wherein the first treatment line is provided with a first intermediate treatment tank disposed between the first and third main treatment tanks and the second treatment line is provided with a second intermediate treatment tank disposed between the second and third main treatment tanks; and the process further comprises a step of transferring the biological liquid from the first main treatment tank to the first intermediate treatment tank and the steps of incubating and adjusting pH to approach a target pH in the first treatment line take place in the first intermediate treatment tank; as well as a step of transferring the biological liquid from the second main treatment tank to the second intermediate treatment tank and the steps of incubating and adjusting pH to approach a target pH in the second treatment line take place in the second intermediate treatment tank.

\* \* \* \* \*